US011193109B2

(12) United States Patent
Zorin et al.

(10) Patent No.: US 11,193,109 B2
(45) Date of Patent: Dec. 7, 2021

(54) BIOTRANSPLANT FOR TREATING GUM RECESSION AND RESTORING GINGIVAL TISSUE VOLUME

(71) Applicant: LIMITED LIABILITY COMPANY "VITACEL", Moscow (RU)

(72) Inventors: Vadim Leonidovich Zorin, Moscow (RU); Alla Ivanovna Zorina, Moscow (RU); Elena Ivanovna Gusarina, Saint Petersburg (RU); Pavel Borisovich Kopnin, Moscow (RU); Artur Aleksandrovich Isaev, Moscow (RU)

(73) Assignee: LIMITED LIABILITY COMPANY "VITACEL", Moscow (RU)

( * ) Notice: Subject to any disclaimer, the term of this patent is extended or adjusted under 35 U.S.C. 154(b) by 0 days.

(21) Appl. No.: 17/170,199

(22) Filed: Feb. 8, 2021

(65) Prior Publication Data
US 2021/0180022 A1 Jun. 17, 2021

Related U.S. Application Data

(63) Continuation of application No. PCT/RU2019/000790, filed on Nov. 6, 2019.

(30) Foreign Application Priority Data

Nov. 15, 2018 (RU) .......................... RU2018140214

(51) Int. Cl.
| C12N 5/077 | (2010.01) |
| A61K 35/16 | (2015.01) |
| A61K 35/19 | (2015.01) |
| A61K 35/33 | (2015.01) |
| A61L 27/38 | (2006.01) |
| A61L 27/54 | (2006.01) |
| A61L 27/36 | (2006.01) |
| A61C 8/00 | (2006.01) |
| A61C 1/00 | (2006.01) |

(52) U.S. Cl.
CPC .............. *C12N 5/0656* (2013.01); *A61C 8/00* (2013.01); *A61K 35/16* (2013.01); *A61K 35/19* (2013.01); *A61K 35/33* (2013.01); *A61L 27/3616* (2013.01); *A61L 27/3813* (2013.01); *A61L 27/3865* (2013.01); *A61L 27/54* (2013.01); *A61L 2430/12* (2013.01); *C12N 2533/56* (2013.01)

(58) Field of Classification Search
None
See application file for complete search history.

(56) References Cited

U.S. PATENT DOCUMENTS 6,878,383 B2    4/2005  Boss, Jr. et al.

OTHER PUBLICATIONS

Chisini et al., Acta Stomatologica Croatica, May 2017, 51(2);133-140. (Year: 2017).*
Tsai et al., J Dent Sci, 2009, 4(3):130-135 (Year: 2009).*
Buduneli N. (2020) Anatomy of Periodontal Tissues. In: Biomarkers in Periodontal Health and Disease. Springer, Cham. https://doi.org/10.1007/978-3-030-37317-7_1 (Year: 2020).*
International Search Report dated Feb. 13, 2020, in International Application No. PCT/RU2019/000790, with English Translation—3 pages.
Written Opinion dated Feb. 13, 2020, in International Application No. PCT/RU2019/00790 3 pages.
Novinki kletochnykh tekhnologii i ikh vozmozhnosti v esteticheskoi meditsine. obtained at http://sprs-therapy.ru/novosti/Novinki-kletochnyh-tehnologii-i-ih-vozmozhnosti-v-esteticheskoi-meditsine.-Estet-Portal on Jan. 25, 2021 with English Summary of Zorin Interview Apr. 18, 2018 9 pages.
Robert Marx, "Platelet-Rich Plasma: Evidence to Support Its Use",*J Oral Maxillofac Surg* , (2004) vol. 62, pp. 489-496.
Ehrenfest et al, "Classification of platelet concentrates: from pure platelet-rich plasma (P-PRP) to leucocyte- and platelet-rich fibrin (L-PRF)", *Trends in Biotechnology* (2008), vol. 27 No. 3, pp. 158-167.
Ebisawa et al, "Gingival and dermal fibroblasts: Their similarities and differences revealed from gene expression", *Journal of Bioscience and Bioengineering*, (2011), vol. III No. 3, pp. 255-258.
Ehrenfest et al, "In Search of a Consensus Terminology in the Field of Platelet Concentrates for Surgical Use: Platelet-Rich Plasma (PRP), Platelet-Rich Fibrin (PRF), Fibrin Gel Polymerization and Leukocytes", *Current Pharmaceutical Biotechnology*, (2012) vol. 12, pp. 1131-1137.
Zorin et al, "Clinical-instrumental and morphological evaluation of the effect of autologous dermal fibroblasts administration", *J Tissue Eng Regen Med* (2014) 9 pages.
Linard et al, "Therapeutic Potential of Gingival Fibroblasts for Cutaneous Radiation Syndrome: Comparison to Bone Marrow-Mesenchymal Stem Cell Grafts" *Stem Cems and Development*, 2015, vol. 00, No. 00, pp. 1-12.
Milinkovic et al, "Clinical application of autologous fibroblast cell culture in gingival recession treatment", *J Periodont Res*, (2015) vol. 50: pp. 363-370.
Häkkinen et al, "Distinct phenotype and therapeutic potential of gingival fibroblasts", *Cytotherapy*, (2014) vol. 16, pp. 1171-1186.
Mah et al, "Human gingival fibroblasts display a non-fibrotic phenotype distinct from skin fibroblasts in three-dimensional cultures", *PloS One.*,(2014) vol. 9, No. 3, 20 pages.

(Continued)

*Primary Examiner* — Allison M Fox
(74) *Attorney, Agent, or Firm* — Oblon, McClelland, Maier & Neustadt, L.L.P.

(57) ABSTRACT

Provided is a method for making a biotransplant, comprising introducing autologous fibroblasts isolated from an oral mucosa of a patient into a platelet-rich fibrin (PRF) membrane using linear retrograde needle injection, where a needle is inserted into a thickness of the PRF membrane and a first puncture is made and then a series of punctures are made that are linearly aligned or arrayed with the first puncture and are spaced at a predetermined distance from a prior puncture. A method of treatment of a periodontal tissue and a biotransplant comprising a PRF membrane and autologous fibroblasts are also provided.

16 Claims, 11 Drawing Sheets

(56) References Cited

OTHER PUBLICATIONS

McGuire et al, "A randomized, double-blind, placebo controlled study to determine the safety and efficacy of cultured and expanded autologous fibroblast injections for the treatment of interdental papillary insufficiency associated with papilla priming procedure", *J Periodontol*, (2007) vol. 78, pp. 4-17.
Fournier et al, "Gingiva as a source of stem cells with therapeutic potential", *Stem Cells Dev.*, (2013), vol. 22, 71 pages.
Grudyanov et al, "Use of autogenous fibroblasts of human oral mucosa for gum recession treatment", *Stomatologiya*, 1 (2013), 8 pages w/ English abstract.
Borie et al, "Platelet-rich fibrin application in dentistry: a literature review", *Int J Clin Exp Med*, (2015) vol. 8 No. 5, pp. 7922-7929.
Grudjanov et al, "Cell technologies in periodontology", Stomatology, 2009; vol. 1, pp. 71-73.

* cited by examiner

| Antigen | GF, % |
|---|---|
| CD34 | <0.5 |
| CD45 | <0.5 |
| CD73 | >99 |
| CD90 | >99 |
| CD105 | >99 |
| Collagen I | >95 |
| Collagen III | >95 |
| Elastin | >95 |
| Vimentin | >95 |
| Cytokeratins 14-16, 19 | <0.5 |

BIOTRANSPLANT FOR TREATING GUM RECESSION AND RESTORING GINGIVAL TISSUE VOLUME

CROSS REFERENCE TO RELATED APPLICATIONS

This application is a continuation application of International application PCT/RU2019/000790, filed Nov. 6, 2019, which claims priority to application RU2018140214, filed Nov. 15, 2018, the entire contents of which are hereby incorporated herein by reference.

BACKGROUND OF THE INVENTION

Field of Invention

The invention relates to medicine, namely dentistry, and concerns medicinal preparations for periodontal soft tissue restoration and methods of their production.

Discussion of the Background

Nowadays, "the gold standard" for closing gingival recessions is the use of the connective tissue transplant ("CTT") in combination with one of the mucogingival surgery techniques (coronally displaced flap or laterally displaced flap). However, the use of these methods may be accompanied by such symptoms as pain in the transplant collection area and in the operation area, as well as inflammation, bleeding, possible necrosis of the flap, infection in the donor area, additional trauma to the patient at the transplant collection site, and a rather long period of rehabilitation [1].

In this regard, many research groups are currently actively searching for methods of closing gingival recessions that would not be inferior to CTT in application and clinical efficacy and would not be accompanied by the abovementioned side effects.

Methods of regenerative medicine are of particular interest, whereas the success of tissue engineering and the results of the study of stem/differentiated cells provide grounds for the development of new approaches to restore the volume of the attached gingiva, the main task of which is to replace or restore lost tissues through transplantation of cells obtained in vitro, in particular, fibroblasts of the oral mucosa [2-6]. To reconstruct periodontal soft tissues, a number of researchers have suggested using fibroblasts of the human oral mucosa immobilized on various carriers, for example, on the collagen membrane [7-11]. A major disadvantages of using such carriers for reconstructive periodontal surgery are their evident "shrinkage", low adaptive properties (due to their foreign origin), a long healing period, and an unexpressed clinical result.

In recent years, clinicians have been interested in using autologous matrices obtained, for example, from PRP (Platelet-Rich Plasma of the blood) in surgical dentistry, periodontics, and implantation. In addition, growth factors and cytokines contained in PRP have distinct reparative properties [12, 13]. Thus, the results obtained by dental surgeons, periodontists, and maxillofacial surgeons using such medicinal products have demonstrateda pronounced clinical effect of the restoration of soft and hard periodontal tissues [14-16].

One of these products is PRF (Platelet-Rich Fibrin) obtained from patient's blood plasma, which is a dense fibrin network enriched with platelets and white blood cells [17]. Due to its structural features, PRF provides not only long-term release of growth factors (VEGF, IGF1, and PDGF-AB) and cytokines (IL-1b), but also provides pronounced cell migration [18] and osseointegration, which is clinically manifested by faster healing of the operated hard and soft tissues and by lowering the postoperative discomfort [16, 19]. High PRF biocompatibility with the patient's tissues has been also shown, as PRF has been obtained from autologous biomaterial, patient's blood, without using anticoagulants [20].

The literature presents the data demonstrating a positive effect of PRP preparations, including PRF, on fibroblasts of the human oral mucosa, which is manifested in the activation of migration and proliferation of these cells, as well as in the increase of collagen synthesis by the cells [20, 21].

The obtained data suggest that the use of PRP preparations and fibroblasts of the human oral mucosa can be clinically effective for filling the lost volumes of soft tissues and eliminating gingival recessions.

The oral mucosa fibroblasts (MF) are cells of the mesenchymal origin representing a main cellular component of the gingival connective tissue plate providing its homeostasis, morphofunctional organization and realizing its physiological and reparative potential [22-25]. In culture, fibroblasts actively produce procollagen, proelastin, glycosaminoglycans, growth factors, and other components of the extracellular matrix [23-25]. After transplantation of the cultured fibroblasts into the connective tissue, their activity is maintained [6, 24].

Autologous MF (autoMF) do not conflict with the patient's own immune system and do not cause allergic or other adverse reactions. A positive clinical effect from using autoMF is due to their high therapeutic activity, e.g., production of extracellular matrix components, including collagen, elastin, growth factors, and cytokines; acceleration of angiogenesis; proliferation of capillary endothelial cells; and thus, increased regeneration of damaged periodontal tissues [23, 25, 26].

There is a known method for correcting soft tissue defects by using autologous skin fibroblasts together with various forms of collagen and glycosaminoglycans (U.S. Pat. No. 6,878,383, IPC A61A 13/00) [27].

This method has a number of disadvantages:

(1) The use as a carrier of foreign collagens and glycosaminoglycans cross-linked with glutaraldehyde. When this biomaterial biodegrades, monomeric glutaraldehyde can be released into the body tissues and fluids, which can have a cytotoxic effect on fibroblasts and cause the development of unexpected side effects [28];

(2) The use of skin fibroblasts as a cellular component.

It has been shown that fibroblasts maintain their specific pattern of the NOX gene expression, i.e., a "topographical code" that determines tissue specificity of cell functions and their interaction with other cells [29]. Thus, a comparative analysis of oral mucosa fibroblasts, in particular, gingival fibroblasts (GF) and skin fibroblasts (SF) of a human face, including the analysis of gene expression profiles, has revealed that these two types of fibroblasts have noticeable differences [29, 30]. There is a significant difference in the expression of 278 genes (totally, 5284 genes have been analyzed), mainly associated with ECM (extracellular matrix), oxidoreductases, growth factors/cytokines [31]. Differences were also found (in vitro and in vivo) in the amount of ECM components secreted by cells (elastin, collagen types I, III, and V, fibronectin, periostin, osteopontin, hyaluronan, cysteine-rich protein 1, thrombospondins, sulfated glycosaminoglycans, heparin, chondroitin, dermatan and keratan sulfate, small leucine-rich proteoglycans and tenascins) [32, 33].

Accordingly, significant differences were also observed between the niches created by GF and SF in ECM, which play a key role in the implementation of their functions [34]. At the same time, it has been shown that GF have a high ability to reduce inflammation, significantly surpassing SF in this process [35, 36]. In comparison with SF, GF produce more osteoprotegerin (osteoclastogenesis inhibitory factor) and less osteoclastogenic factors, which, therefore, leads to the weakening of osteoclastogenic processes promoting bone resorption [37]. GF produce large amounts of matrix metalloproteinases that regulate the activity of inflammatory mediators and their inhibitors [38]. Compared to SF, GF are less sensitive to the profibrogenic action of growth factor TGF-β1 that stimulates development of fibrosis and scarring [25, 30, 39]. In contrast to SF, GF are "programmed" for rapid completion of the inflammatory process and ECM remodeling accompanied by neoangiogenesis, which contributes to rapid wound healing without scarring. Apparently, this GF ability may be explained by the peculiarities of their origin [25, 32, 40, 41].

It has been shown that when transplanted into the gingiva, fibroblasts isolated from the oral mucosa induce formation of the keratinized gingiva epithelium that is identical to the normal epithelium of this tissue [32, 42]. They have a high potential for stimulating epithelial tissue development and regulating expression of cytokeratins in the epithelial cells [43], while having a significant effect not only on epithelial morphogenesis, but also on the structure of the epithelial tissue. In particular, the results of experiments on tissue and cell recombination confirm the fact that formation of epithelial phenotypes of the oral mucosa directly depends on the connective tissue located below it and its constituent fibroblasts [32].

A comparative study of GF and SF (which are often used for healing skin wounds of various origin) has shown that these two types of fibroblasts almost are not different from each other in their ability to contract collagen and fibrin gel in vitro (this is a common method for studying functional activity of fibroblasts) [33]. However, it has been noticed that GF have higher ability to migrate and embed into a three-dimensional collagen matrix due to their rapid and intensive secretion of PDGF (platelet-derived growth factor) that stimulates cell migration [44]. Owing to this effect, GF quickly "populate" the granulation tissue formed during wound healing. The expressed ability of GF to reduce and destroy fibrin fibers at the early stages of healing due to the increased expression of a plasminogen activator [45] likely allows these cells to quickly rebuild ECM, thereby accelerating the reparative processes in the wound [46].

Taking into account available data, one can conclude that oral mucosa fibroblasts (MF) are intensively used in preclinical and clinical studies to restore soft tissue defects both inside and outside the oral cavity.

Thus, good clinical results have been obtained by using autologous MF (autoMF) in dental practice to eliminate recessions of the gingiva and to increase its density when the thin gingiva biotype is observed in humans, while these cells were introduced into the gingiva by injections of the cell suspension [6]. Prato G. et al. (2003) presented the results of a pilot study with participation of 6 patients with the thin gingiva biotype in which autoGF were injected into the patient's gingiva in combination with hyaluronic acid as a carrier. The results showed a noticeable increase in the gingiva thickness [47].

The correction of vocal cord scarring with the use of autoGF performed by Chhetri D. with colleagues (2011) on five patients was also efficient [48].

AutoGF were also used to repair vascular walls in rabbits with carotid artery aneurysms. When GF were transplanted into the artery walls, a significant decrease in size of the defect region was observed, while in the control group (using a culture medium or SF), the defect region continued to increase. At the same time, the presence of transplanted cells was detected in the damaged tissues for a long time [36].

Linard S. et al. (2015) showed that transplantation of human GF into the skin of immunodeficient mice to treat radiation wounds caused by local skin irradiation leads to a rapid formation of the completely restored dense epidermis, skin appendages, and hair follicles. It has been noticed that the transplanted GF significantly reduced the inflammatory process caused by irradiation [49].

Therefore, there still exists a need for a better and more efficient biotransplant that can serve as an alternative to CTT completely restoring defects in periodontal soft tissues, in particular, gingival recessions, and increasing the volume, as well as a method for obtaining the biotransplant and a method for treating periodontal diseases.

BRIEF DESCRIPTION OF THE FIGURES

The patent or application file contains at least one drawing executed in color. Copies of this patent or patent application publication with color drawing(s) will be provided by the office upon request and payment of the necessary fee.

A more complete appreciation of the invention and many of the attendant advantages thereof will be readily obtained as the same becomes better understood by reference to the following detailed description when considered in connection with the accompanying drawings, wherein.

SUMMARY OF THE INVENTION

Figures 1, 2:
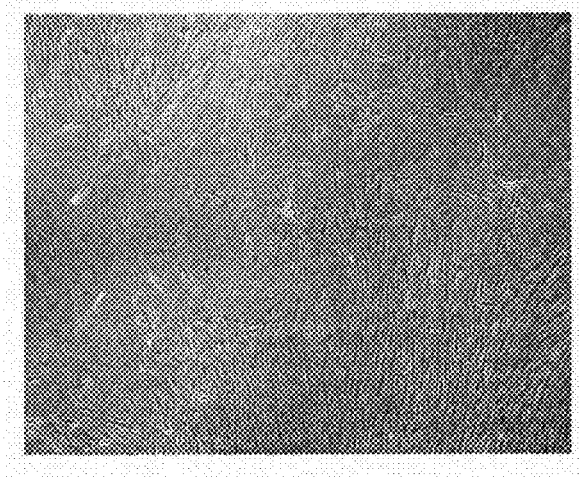
FIG. 1 shows fibroblast-like cells of the oral mucosa (phase-contrast microscopy ×200).
FIG. 2 illustrates immunophenotype of the human oral mucosa fibroblasts.

Accordingly, one object of the present invention is to provide an efficient biotransplant that can serve as an alternative to CTT completely restoring the defects in periodontal soft tissues, in particular, gingival recessions, and increasing the volume, as well as a method for obtaining the biotransplant and a method for treating periodontal diseases.

In one embodiment, a method for making a biotransplant is provided, comprising introducing autologous fibroblasts isolated from an oral mucosa of a patient into a platelet-rich fibrin (PRF) membrane, thereby producing the biotransplant.

In another embodiment, the autologous fibroblasts are suspended in a suitable medium at a concentration of $5 \times 10^6$ to $20 \times 10^6$ cells/ml, and the introducing comprises linear retrograde needle injection of the autologous fibroblasts into the PRF membrane.

In yet another embodiment, the autologous fibroblasts are suspended in a suitable medium at a concentration of $5 \times 10^6$ to $20 \times 10^6$ cells/ml, and the introducing comprises linear retrograde needle injection of the autologous fibroblasts into the PRF membrane. The retrograde needle injection comprises inserting a needle into a thickness of the PRF membrane and making a first puncture and then a series of punctures linearly aligned or arrayed with the first puncture each spaced at a distance of 0.2 to 0.33 mm from a prior puncture, wherein an amount of 50 to 100λ of a 1 ml suspension of the autologous fibroblasts is injected into each puncture until an entire amount of the 1 ml suspension has been injected into the punctures.

In a different embodiment, the autologous fibroblasts are obtained from cryopreserved autologous fibroblasts. The autologous fibroblasts can be further obtained from a biopsy sample of the oral mucosa of the patient. Yet, the autologous fibroblasts can be further obtained from cryopreserved autologous fibroblasts.

In another embodiment, a method of treatment of a periodontal tissue is provided, comprising introducing a biotransplant obtained by the method of claim 1 into a damaged part of the gingiva using a surgery.

In another embodiment, a method for treating a periodontal tissue is provided comprising grafting a biotransplant comprising a PRF membrane and autologous fibroblasts over a periodontal tissue of a subject in need thereof.

In another embodiment, the periodontal tissue comprises a damaged hard gingival tissue, soft gingival tissue, or a combination thereof. Yet, the periodontal tissue can be tissue that has been damaged by oral surgery. The periodontal tissue can comprise a gingival recession or a gingival wound or burn.

In one embodiment, a subject has insufficient connective tissue in the palate for a connective tissue transplant ('CTT'). In another embodiment, the subject has connective tissue in the palate which is too thin to transplant. The subject can have periodontitis, or/and has trauma of tissues around an exposed root of a tooth, and/or has trauma of periodontal tissues around an implant.

In another embodiment, the subject is in need of soft tissue augmentation prior to orthodontic treatment. In another embodiment, the subject exhibits allerological alertness to proteins of foreign origin.

In one embodiment, the autologous fibroblasts are mucosal fibroblasts (autoMF).

Another object of the invention is to provide a biotransplant comprising a PRF membrane and autologous fibroblasts. The autologous fibroblasts can be mucosal fibroblasts.

DETAILED DESCRIPTION OF THE INVENTION

As noted above, an object of the present invention is to provide an efficient biotransplant for completely restoring defects in periodontal soft tissues such as gingival recessions and increasing the volume. The present invention further sets forth a novel method for obtaining the biotransplant and a method for treating periodontal diseases. Autologous fibroblasts of the oral mucosa (autoMF) have been chosen as a cell material used in the present invention.

To complete the task, a biotransplant manufacturing technology has been developed, which includes obtaining PRF (platelet-rich fibrin) in the membrane form by using patient's venous blood and integrating autologous (patient's own) fibroblasts isolated from the patient's oral mucosa into the PRF membrane.

To obtain autoMF, a biopsy sample of the mucosa was taken in the palate area. The biopsy sample of the oral mucosa was taken under local anesthesia (Sol. Ultracaini DC) in the patient's palate area at the level of 6-7th teeth, provided that the patient has no contraindications, including the presence of infectious and oncological diseases, autoimmune diseases of connective tissues, acute and acute chronic periodontal diseases.

The obtained biopsy sample was used to isolate autoMF in a specialized laboratory by the known method [50] with the minor modifications. For this purpose, the biopsy sample was incubated for 6 to 8 hours in DMEM culture medium (PanEco) containing antibiotics (penicillin of 100 U/mL, streptomycin of 100 μg/mL, and gentamicin of 200 μg/mL) and antimicotic amphotericin b (25 μg/mL). After that, the biopsy sample was transferred into DMEM culture medium containing 10% fetal bovine serum (FBS, PanEco), gentamicin of 40 μg/mL, and collagenase type II of from 400 to 500 μg/mL. The biopsy sample was incubated with collagenase at 37° C. for 12 to 16 hours. Then the resulting cell suspension was centrifuged in phosphate-buffered saline (Hank's solution, Biolot) at 300 g for 8 minutes. The resulting cellular precipitate was resuspended in the DMEM culture medium containing from 10 to 20% FBS (or human cord blood serum, or patient's autologous blood serum) and gentamicin (40 μg/mL) and explanted into culture vials T-25 (Nunc). The vials were placed in a $CO_2$ incubator (37° C., 5% $CO_2$) and cultured for from 1 to 3 weeks until the primary culture was obtained (to cultivate autoMF, a serum-free full growth medium for cultivation of fibroblasts [Fibroblast Basal Medium, BioWhittaker Inc., USA], or other similar serum-free media for cultivation of fibroblast-like cells can be also used). Before using FBS, FBS lots were tested for the colony-formation efficiency (CFE-F) and only lots with high CFE-F were selected.

Then the cells were removed from the surface of a cultural vial using a trypsin-EDTA solution and transferred to a new cultural vial T-75 (Nunc) containing a nutrient medium (DMEM, 10-15% FBS). The cells were incubated for a week in a $CO_2$ incubator (37° C., 5% $CO_2$). The nutrient medium was changed every 48-72 hours. As the cells grow and reach a subconfluent layer, they are removed from the surface of the culture vial with a trypsin-EDTA solution (PanEco) and transferred to a new cultural vial of a larger surface (T-150, T-175, or T-500 factory with a triple bottom [Nunc]). When the cells reached a subconfluent monolayer, the culture medium containing 10-20% FBS was replaced with a medium containing 10% autologous patient's serum or a serum-free medium and the cells were incubated for at least 18 hours at 37° C. The use of the serum-free medium for incubating cells allows the removal of foreign proteins contained in FBS. Then the cells were removed from the surface of the cultural vial using the trypsin-EDTA solution, washed three times by centrifugation in the 0.9% sodium chloride solution and suspended in the 0.9% sodium chloride solution used for injections. The resulting cell preparation was an autoMF suspension in the saline solution at a concentration of from 5 or more, 10 or more, and $20 \times 10^6$ cells/mL or less.

The obtained autoMF suspension was incorporated into the autologous PRF membrane that is a pharmacologically acceptable biocompatible biodegradable carrier.

The number of biotransplants depends on the number of gingival defects which is individual for each patient.

A part of the patient's autoMF obtained after the 1st passage was subjected to cryopreservation in a cryoprotection medium (50% DMEM, 40% FBS, 10% DMSO) in concentration of $1.5 \times 10^6$ cells/mL, and the autoMF can be stored in liquid nitrogen indefinitely. This allows one to create, for each patient, the individual master bank, which can be used later, if necessary, to create a biotransplant for restoring patient's periodontal tissues.

The used cell material was subjected to the mandatory testing to exclude viral and bacterial infections, as well as to conduct the cell karyotyping.

Having generally described this invention, a further understanding can be obtained by reference to further certain specific examples which are provided herein for purposes of illustration only and are not intended to be limiting unless otherwise specified.

EXAMPLES

All procedures for obtaining cell biotransplants were performed under GMP, GDP, and GLP conditions.

Figure 3:
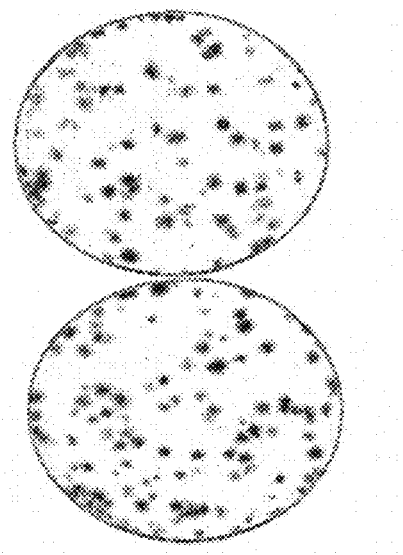
FIG. 3 provides a test for determining colony-forming units of fibroblasts (CFU-F). Colony-forming efficiency of fibroblasts (CFE-F) was determined by the formula: the ratio of the number of formed colonies to the number of explanted cells ×100%. The average CFE-F value for MF was 47-55%.

To characterize the obtained cells, their morphology was studied using phase-contrast microscopy (FIG. 1) and their immunophenotype was determined by analyzing cells with a flow cytometer (FACS Canto™ II) using FACSDiva™ software (Becton Dickinson, USA) and mouse monoclonal antibodies (BD Pharmingen™, USA) obtained against the markers of hematopoietic (CD34, CD45), mesenchymal (CD73, CD90, CD105), and epithelial cells (pancytokeratins 14, 15, 16, and 19) (FIG. 2). In addition, a test for CFU-F (colony-forming units of fibroblasts) was performed (FIG. 3); the colony-formation efficiency (CFE) was determined; specific cell staining for actin F was conducted; and cell lysates were analyzed by Western blotting for collagen type I expression. The expression of specific fibroblast markers (collagen type I and III, elastin, and vimentin) was determined by immunofluorescent analysis using primary monoclonal antibodies and secondary anti-species antibodies labeled with rhodamine by means of an Axioplan™ 200 microscope with an Axiocam™ HRm camera and AxioVision™ software (Carl Zeiss, Germany).

Figure 4:
FIG. 4 shows the PRF membrane.

To obtain the PRF membrane that is a part of the biotransplant, the blood (10 ml) was taken from the patient's cubital vein. Then PRF was obtained in the form of the blood clot using the specialized centrifuge (e.g., Scilogex, USA [RU No. RZN 2015/3442]) according to the suggested manufacturer instructions. The PRF membrane was prepared from the clot by placing it under the press (a box for formation of the membrane is included in the commercial kit) (FIG. 4).

Figure 5:
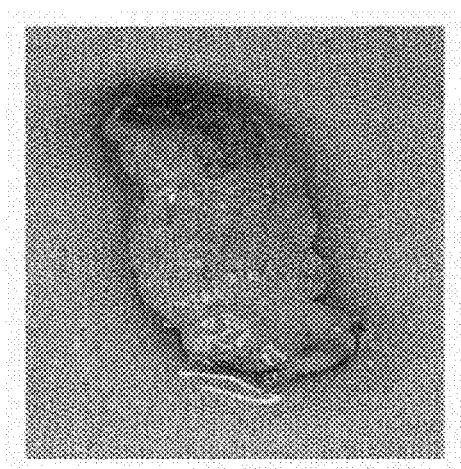
FIG. 5 shows the PRF membrane with incorporated fibroblasts.

To manufacture the biotransplant, the autoMF suspension was introduced into the resulting PRF membrane in concentration of 20 (5, 10, or 15)$\times 10^6$ cells/mL using a needle (30G, 13 mm). For this purpose, the needle was inserted into the membrane thickness to its full length; after that, the autoMF suspension was introduced by the linear-retrograde method (each puncture contained from 50 to 100 µL of the suspension and any intermediate points and ranges). Then the needle was removed and a new puncture was made in parallel to the previous one at the distance of from 0.2 to 0.3 mm; and this should be done until the entire amount of the cell suspension will be introduced (FIG. 5).

Fibroblasts are substrate-dependent cells with the high adhesion to the substrate [6, 22, 24]. The viability of autoMF integrated into the PRF-membrane (in particular, into the A-PRF membrane obtained using a Scilogex centrifuge, USA [RU No. RZN 2015/3442]), which was studied by the inventors using a fluorescent analysis by mean of GFP (Green Fluorescent Protein). For this purpose, the patient's MF were labeled with GFP (using s specialized genetic engineering construct) before they were inserted into the PRF membrane. Then the labeled MF were injected (as described above) into the PRF membrane obtained from patient's blood. The resulting biotransplant was incubated at room temperature for one hour; after that, a total cross-section of the biotransplant was prepared using a microtome and fluorescent analysis was performed.

Figure 6:
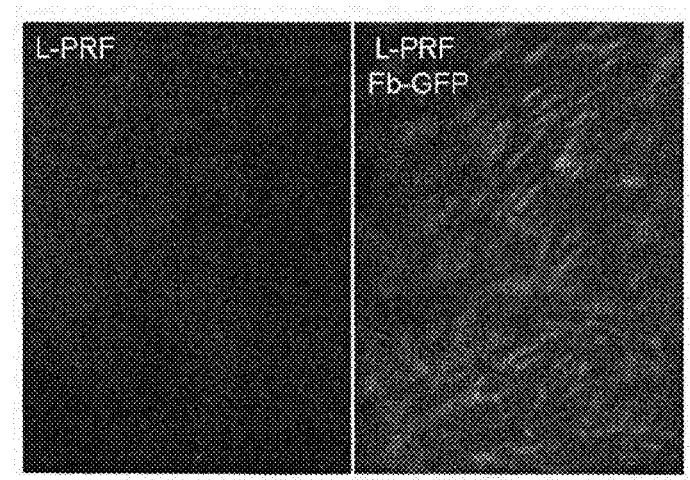
FIG. 6 provides the determination of the viability of oral mucosa fibroblasts. GFP detection in live human MF incorporated into the PRF membrane (fluorescence microscopy).

The results of this study have demonstrated the occurrence of a significant amount of a fluorescent protein in the analyzed section of the biotransplant, which indicates the presence of viable MF in this biotransplant (FIG. 6). The obtained data allowed to conclude that the autoMF were completely integrated into the PRF membrane and maintained their viability.

The use of the PRF membrane as a biotransplant carrier that is biodegradable and biocompatible [20] with the patient's tissues allows to optimize delivery of the autoMF to the defect region of periodontal soft tissues, as well as to maintain the autoMF localization at the site of the tissue defect and to ensure the production of physiologically important content of ECM components. After the transplantation, autoMF (as well as skin autofibroblasts) fully survive in the tissue [6, 24] and efficiently repair the defects of this tissue producing ECM components [6, 24-26].

Surgical intervention in the periodontium was conducted according to the following algorithm. The modified intrasulcular incision was made in the area of gingival recession. Then the split mucoperiosteal flap was formed. After that, the root surface was prepared using periodontal curettes and de-epithelization of the interdental papillae was performed.

The obtained biotransplant consisting of the PRF membrane containing the integrated patient's autoMF was fixed by means of nonresorbable surgical threads (Prolene™ 6.0) to the interdental papillae of the gum, covering the exposed surface of tooth roots. After that, the flap was mobilized and fixed in the interdental spaces, completely closing the introduced biotransplant. For suturing the wound, nonresorbable sutures (Prolene™ 6.0 and 7.0) were used. In the area of the transition fold, "anchor" sutures were applied. The sutures were removed after 12 to 14 days.

The biotransplant of the invention has a consistency that is convenient for surgical intervention and provides low trauma, rapid patient rehabilitation, and simple handling in addition to the considerable clinical effect.

The present invention provides a method for obtaining a biotransplant, a method of using the biotransplant, and means of creating an individual patient's autoMF master bank, which allows one to conduct surgical intervention for the patient multiple times, depending on the number and size of the defect(s) without a multiple taking biopsy samples of soft tissue biomaterials of the oral cavity.

To obtain PRF, different centrifuges were used from various manufacturers (Scilogex, USA [RU No. RZN 2015/3442], Regen-PRP-Centri, Switzerland [RU No.FSZ 2012/13228]) (see Clinical case examples), and the resulting PRF membranes differ in the density of the fibrin network. Thus, the PRF membrane obtained using Scilogex centrifuges (USA) is the densest one, which makes it the most convenient for doctors when using it for the biotransplant preparation and performing procedures.

It should be noted that differences in the membrane density have not influences the course of the postsurgical period and the manifestation of the clinical effect. Thus, when obtaining the biotransplant, one can use the PRF membrane from any manufacturer.

Main advantages of the present invention (in comparison to all other methods that are currently available in this field) are the following: (1) the use of particular autologous components obtained from patient's tissues, which eliminates the risk of the biotransplant rejection or any other immune reactions; (2) low traumaticity of taking a tissue biopsy sample and conducting surgical intervention; (3) the postsurgical period is not accompanied by discomfort for the patient and proceeds without edema, bruising, and pain.

In terms of the clinical efficiency and stability of the result, the use of the biotransplant (the PRF membrane+autoMF) not only corresponds to the use of CTT ("gold standard"), but also has a number of advantages: the faster tissue healing in the postsurgical period (the minimal sensation of pain, the absence of edema and hematomas), which allows one to remove sutures 2 days earlier (after 10 to 12 days vs. 12 to 14 days); the average percentage of closing the gingival recessions is 95% while closing the class I and II recessions (according to Miller's scale) is 100%; the formation of attached tissues occurs along the border of the enamel-cement connection, while using CTT may cause an excessive overlap of this border; the formation of tissues that are uniform in thickness and color, while using CTT results in the uneven contour of tissues.

The present invention can be used for:
closing the generalized gingival recessions, when there is not enough tissue volume to take CTT from the palate (for example, when implants are installed in the area of chewing teeth in the upper jaw);
thin phenotype of the periodontal tissues, when it is not possible to take a CTT sample from the palate to close gingival recessions due to insufficient tissue thickness in this area;
trauma of the attached tissues in the area of the exposed tooth roots in patients with periodontitis at the stage of remission, since this group of patients does not have enough connective tissue in the palate to take a transplant;
soft tissue augmentation before orthodontic treatment in young patients (16-20 years old) who have thin periodontal phenotype and distinct prominence of the roots;
formation of attached tissues and gingival recession plastics in patients with high allergological alertness, especially to proteins of the foreign origin.

The comparative analysis of clinical efficiency of the PRF membrane (Clinical case No. 1, A) and the PRF membrane+autoMF (the biotransplant) (Clinical case No. 1, B) revealed the significant advantage of the biotransplant use, which was in the faster healing process after surgery and the complete closing of gingival recessions. When only PRF was used, the healing process was slower with more pronounced clinical manifestations (e.g., pain, edema) and only a slight increase in the tissue thickness was observed with the minimal closing of the gingival recessions (1-2 mm).

The obtained data allowed to conclude that the using the PRF membrane+autoMF is preferred compared to when the PRF membrane alone for closing gum recessions is used.

Apparently, autoMF introduced into the area of the gingival defect produce collagen and other ECM components and thus stimulate restoration of the lost gum volume, which in turn leads to the closure of the gingival recessions while the PRF membrane serves as an optimal carrier for autoMF.

Clinical Case Example No. 1 (A, B)

Figure 7A:
FIG. 7 A, B, C. Clinical case no. 1 (A). The use of the PRF membrane alone to close gingival recessions: (A) Before treatment, (B) 14 days after surgery, (C) 3 months after surgery.
Figure 7B:
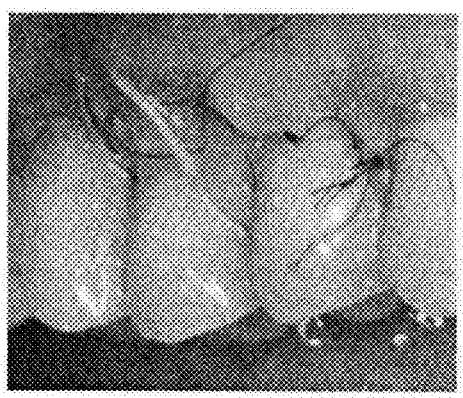
Figure 7C:

A. The use of the PRF membrane for closing the gingival recessions (FIG. 7, A, B, C).

Patient B., 49 years old. Diagnosis: Generalized recessions in the upper jaw tooth area of class I-II according to Miller's scale.

The patient underwent surgery in the area of gingival recessions (15-14) using the PRF membrane obtained with a Scilogex centrifuge, USA (RU No. RZN 2015/3442) (the method was described above, FIG. 4).

Clinical results: during the first 3 days, the patient noted discomfort accompanied by edema and pain; the sutures were removed 14 days after surgery; a slight increase in the volume of the gums and a slight closure of the recessions (no more than 1-2 mm) was observed in 3 months after the surgery.

Figure 8A:
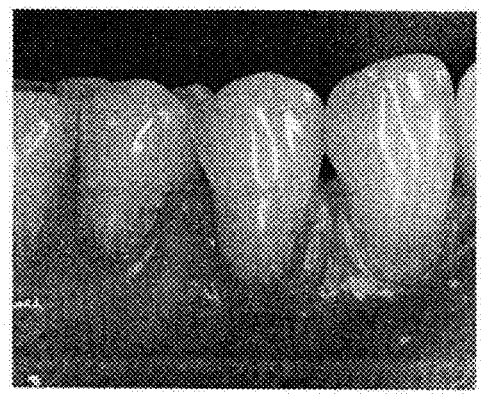
FIG. 8 A, B, C. Clinical case no. 1. (B). Surgical intervention into the area of gingival recessions using the PRF membrane+autoMF: (A) Before treatment, (B) 12 days after surgery, (C) 3 months after surgery.
Figure 8B:
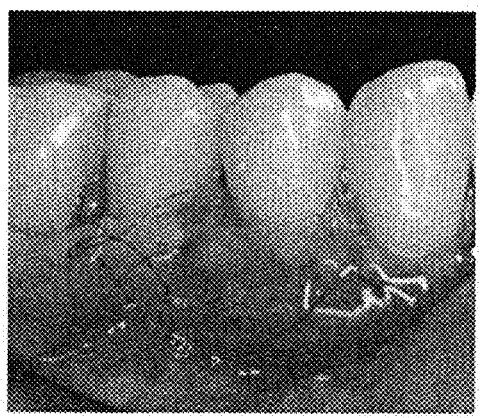
Figure 8C:
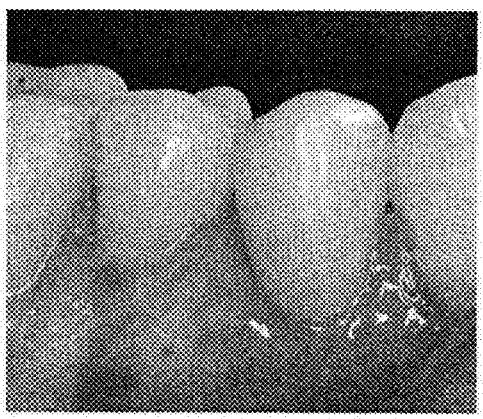

B. The use of the PRF membrane+autoMF for closing the gingival recessions (FIG. 8 A-B).

Patient A., 42 years old. Diagnosis: Generalized recessions in the lower jaw tooth area of the class I-II according to Miller's scale.

The patient underwent surgery in the area of gingival recessions in the similar A zone using the PRF membrane obtained with a Scilogex centrifuge, USA (RU No. RZN 2015/3442) while the membrane contained autoMF (the method was described above, FIG. 5).

Clinical results: the postsurgical period was not accompanied by discomfort, minor edema was observed only during the first day after surgery; the sutures were removed 12 days after the surgery, the complete closure of the gum recessions was revealed in 3 months after the surgery.

Clinical Case Example No. 2

Figure 9A:
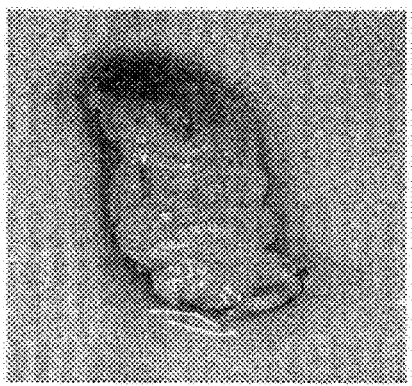
FIG. 9 A-G. Clinical case no. 2. (A) The biotransplant which is the PRF membrane (obtained by using a Scilogex centrifuge, USA (RU no. RZN 2015/3442) with the patient's autoMF integrated into it: (B) Before treatment, (C) Immediately after surgery, (D) 12 days after surgery, (E) One month after surgery, (F) 3 months after surgery, (G) 6 months after surgery.

Patient A., 42 years old, complained of tooth root exposure (3.4-3.7), the increased tooth sensitivity when taking cold liquid and brushing teeth. Objectively: 3.4-3.7-generalized recessions of the class II-III according to Miller's scale (2 to 5 mm). The thin periodontal biotype was observed. Diagnosis: Generalized recessions in the area of 3.4-3.7 teeth of class I-III according to Miller's scale, the thin periodontal biotype was observed (FIG. 9A).

Previously, tissue samples were already taken twice from the patient's palate and the x-ray analysis showed that the tissue volume was insufficient for sampling in the palate. The patient was proposed to perform plastic surgery of the gingival recessions using a biotransplant containing the PRF membrane obtained with a Scilogex centrifuge, USA (RU No. RZN 2015/3442) while autoMF were integrated into the membrane.

For this purpose, a biopsy sample (4 mm$^2$) was taken in the palate area (sector 2, level of tooth 2.6).

AutoMF were isolated from the obtained biopsy sample and a month later delivered to the clinic as a suspension containing $20 \times 10^6$ cells/mL in the saline solution.

The blood (10 mL) was taken from the patient's cubital vein. The blood was used to obtain the PRF membrane using a Scilogex centrifuge, USA (RU No. RZN 2015/3442).

Figure 9B:

The biotransplant was manufactured on the basis of the obtained patient biomaterials. A cell suspension (1 mL) containing autoMF ($20 \times 10^6$ cells) was introduced into the resulting PRF membrane by means of several punctures. For this purpose, a needle was inserted into the membrane thickness to its full length; after that, the autoMF suspension was introduced by the linear-retrograde method (each puncture contained from 50 to 100 μL of the cell suspension). Then the needle was removed and a new puncture was made in parallel to the previous one at the distance of 0.2 to 0.3 mm; and this was repeated until the entire amount of the cell suspension had been introduced (FIG. 9B).

Under the infiltration anesthesia (Sol. Ultracaini DS, carpules 1.7-2), a modified intrasulcular incision was performed in the area of 3.4-3.7 teeth. Then a split mucoperiosteal flap was formed. After that, the root surface was treated using periodontal curettes and de-epithelization of the interdental papillae was conducted.

Figure 9C:
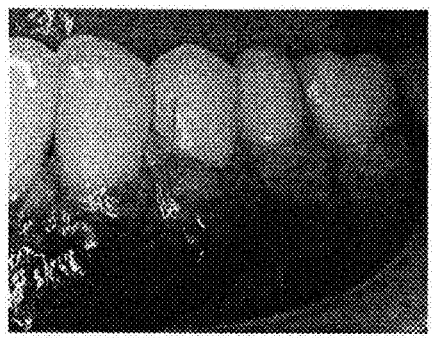

The obtained biotransplant was fixed on the prepared root surface by means of nonresorbable surgical threads (Prolene 6.0). After the mobilization, the flap was fixed with sutures (Prolene 6.0 and 7.0). In the area of the transition fold, "anchor" sutures were applied (FIG. 9C).

After the surgery, the patient received standard recommendations for the postsurgical care of the oral cavity.

On the 4th day, a clinical examination was performed during which no edema and hematomas were observed. According to the patient, she experienced no discomfort or pain during the postsurgical period.

Figure 9D:
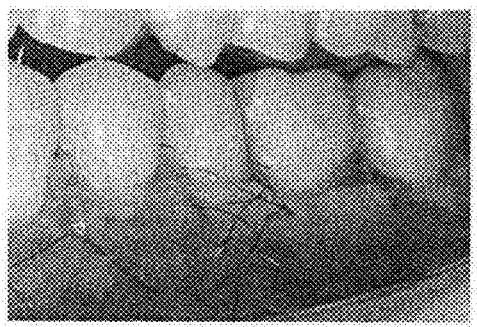
Figure 9E:
Figure 9F:
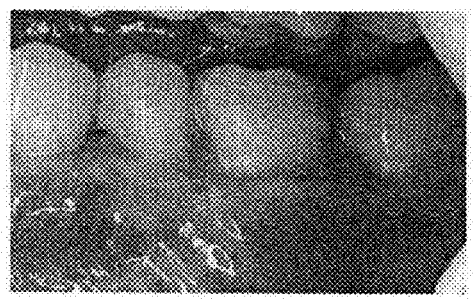
Figure 9G:
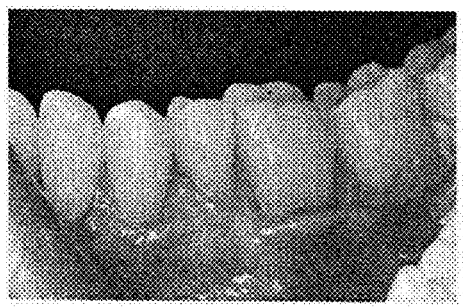

On the 12th day, the sutures were removed (FIG. 9D). Clinically, the increase in the gum thickness and closing of the gingival recessions in the area of 3.4-3.7 teeth was revealed. This clinical picture was also observed after 1, 3, and 6 months of observation (FIG. 9 E, F, G).

No complications and adverse events were detected during the entire period of observation.

Clinical Case Example No. 3

Figure 10A:
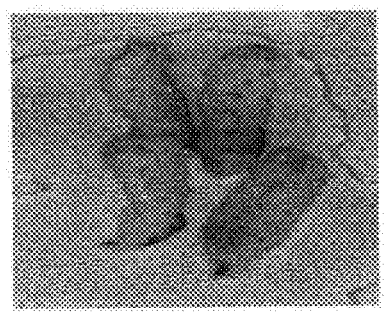
FIG. 10 A-G. (A) Biotransplants which are the PRF membranes (obtained by using a Scilogex centrifuge, USA (RU no. RZN 2015/3442) with the patient's autoMF integrated into them: (B) Before treatment, (C) Immediately after surgery, (D) 12 days after surgery, (E) One month after surgery, (F) 3 months after surgery, (G) 6 months after surgery.

Patient M., 41 years old, complained about tooth root exposure (11-21-22-23-24) and increased tooth sensitivity when taking cold liquids and brushing teeth. Objectively: 11-24 generalized recessions of the class I according to Miller's scale (1 to 3 mm). The thick periodontal biotype was observed. Diagnosis: Generalized recessions in the area of 11-24 teeth of the class I according to Miller's scale (FIG. 10A).

The patient has implants installed in position 25-27; thus it was not possible to take a graft in the donor zone. In this regard, the patient was offered to perform plastic surgery of the gingival recessions using a biotransplant containing the PRF membrane obtained with a Scilogex centrifuge, USA (RU No. RZN 2015/3442) while autoMF were integrated into the membrane.

For this purpose, a biopsy sample (4 mm$^2$) was taken in the palate area (sector 2, level of tooth 2.6).

AutoMF were isolated from the obtained biopsy sample and a month later delivered to the clinic as a suspension containing $20 \times 10^6$ cells/mL in the saline solution.

The blood (32 mL, 4 test tubes of 9 mL each) was taken from the patient's cubital vein. The blood was used to obtain four PRF membranes using a Scilogex centrifuge, USA (RU No. RZN 2015/3442).

Figure 10B:
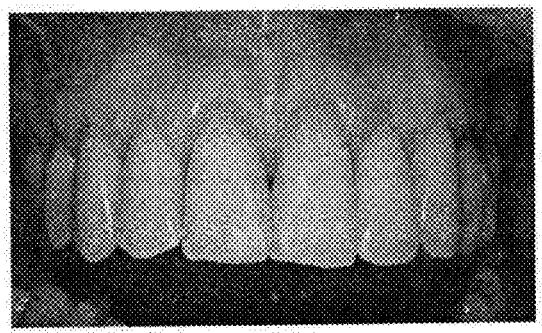

The biotransplants were manufactured on the basis of the obtained patient biomaterials. The cell suspension (1 mL) containing autoMF ($20 \times 10^6$ cells) was introduced into the resulting PRF membrane by means of several punctures. For this purpose, a needle was inserted into the membrane thickness to its full length; after that, the autoMF suspension was introduced by the linear-retrograde method (each puncture contained 50 to 100 μL of the cell suspension). Then the needle was removed and a new puncture was made in parallel to the previous one at the distance of 0.2 to 0.3 mm; and this was repeated until the entire amount of the cell suspension was introduced (FIG. 10B).

Under the infiltration anesthesia (Sol. Ultracaini DS, carpules 1.7-2), the modified intrasulcular incision was made in the area of 11-21-24 teeth. Then a split mucoperiosteal flap was formed. After that, the root surface was treated using periodontal curettes and de-epithelization of the interdental papillae was conducted.

Figure 10C:
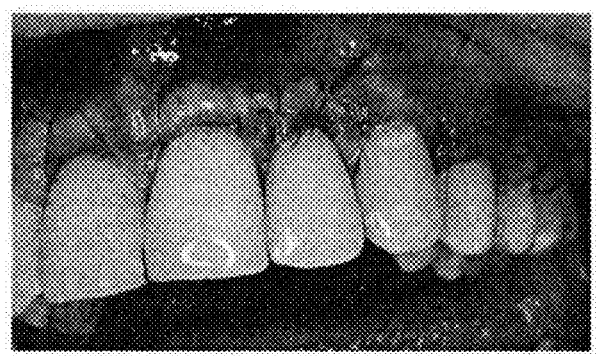

The obtained biotransplants were fixed on the prepared root surfaces using sutures in the interdental spaces. After the mobilization, the flaps were fixed with sutures (Prolene 6.0 and 7.0). In the area of the transition fold, "anchor" sutures were applied (FIG. 10C).

After the surgery, the patient received standard recommendations for the postsurgical care of the oral cavity.

On the 2nd day after the surgery, the patient had a slight swelling of the upper lip which persisted for 2 days, while the pain was minimal.

On the 4th day, a clinical examination was performed and no edema and hematomas were revealed.

Figure 10D:
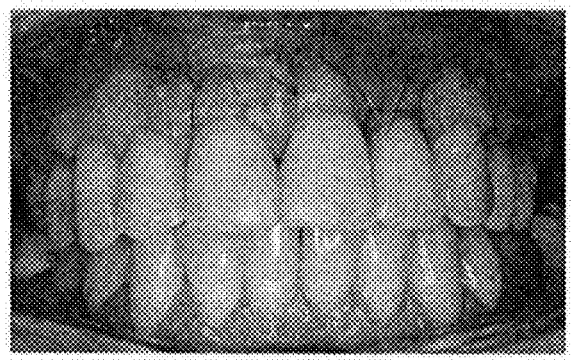
Figure 10E:
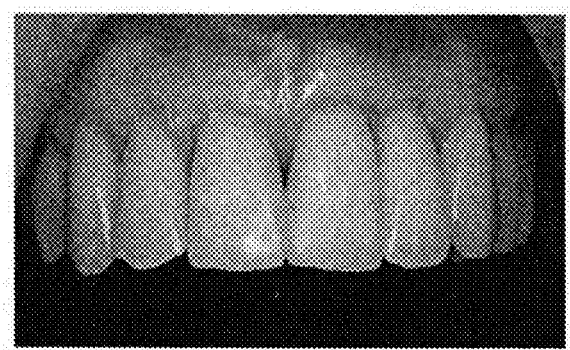
Figure 10F:
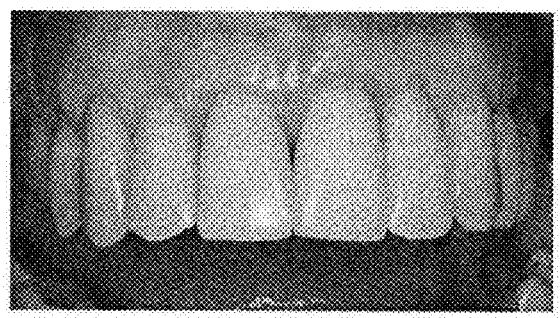
Figure 10G:
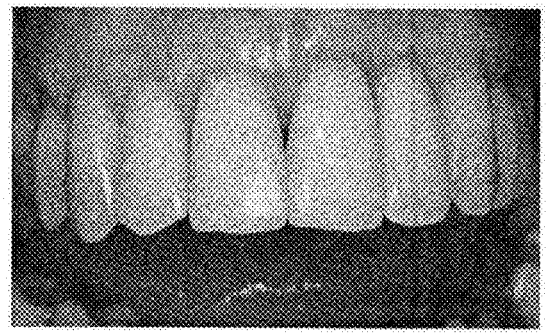

On the 12th day, the sutures were removed (FIG. 10D). Clinically, a closing of the gingival recessions in the area of 11-21-24 teeth was revealed. The same clinical picture was observed after 1, 3, and 6 months of observation (FIG. 10 E, F, G).

No complications and adverse events were revealed during the entire period of observation.

Clinical Case Example No. 4

Patient M., 44 years old, complained of tooth root exposure (13-23) and increased tooth sensitivity when taking cold liquids and brushing teeth. Objectively: 13-23 generalized recessions of the class I-III according to Miller's scale (2 to 4 mm). The thick periodontal biotype was observed.

Figure 11A:
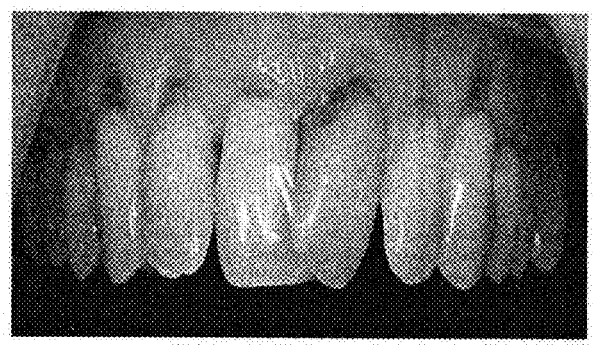
FIG. 11 A-E. Clinical case no. 4. (A) Before treatment, (B) 12 days after surgery, (C) One month after surgery, (D) 3 months after surgery, (E) 6 months after surgery.

Diagnosis: Generalized recessions in the area of 13-23 teeth of the class I-III according to Miller's scale (FIG. 11A).

The patient previously had CTT taken in the palate area; thus there were not enough tissues in the donor area to take the graft. In this regard, the patient was offered to perform plastic surgery of the gingival recessions using the biotransplant containing the PRF membrane obtained with a centrifuge (Regen-PRP-Centri, Switzerland [RU No. FSZ 2012/13228]) while autoMF were integrated into the membrane.

For this purpose, a biopsy sample (4 mm$^2$) was taken in the palate area (sector 2, level of tooth 2.6).

AutoMF were isolated from the obtained biopsy sample and a month later delivered to the clinic as a suspension containing 20×10$^6$ cells/mL in saline solution.

The blood (32 mL, 4 test tubes of 9 mL each) was taken from the patient's cubital vein. The blood was used to obtain four PRF membranes using a centrifuge (Regen-PRP-Centri, Switzerland) (RU No. FSZ 2012/13228).

The biotransplants were manufactured on the basis of the obtained patient biomaterials. The cell suspension (1 mL) containing autoMF (20×10$^6$ cells) was introduced into the resulting PRF membrane by means of several punctures. For this purpose, a needle was inserted into the membrane thickness to its full length; after that, the autoMF suspension was introduced by the linear-retrograde method (each puncture contained 50 to 100 µL of the cell suspension). Then the needle was removed and a new puncture was made in parallel to the previous one at the distance of 0.2 to 0.3 mm; and this was repeated until the entire amount of the cell suspension was introduced.

Under the infiltration anesthesia (Sol. Ultracaini DS, carpules 1.7-2), the modified intrasulcular incision was made in the area of 13-23 teeth. Then a split mucoperiosteal flap was formed. After that, the root surface was treated using periodontal curettes and de-epithelization of the interdental papillae was conducted.

Figure 11B:
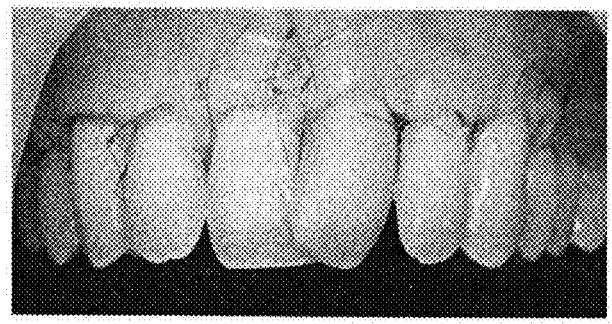

The obtained biotransplants were fixed on the prepared root surfaces using sutures in the interdental spaces. After mobilization, the flaps were fixed with sutures (Prolene 6.0 and 7.0). In the area of the transition fold, "anchor" sutures were applied (FIG. 11B).

After surgery, the patient received standard recommendations for postsurgical care of the oral cavity.

On the 2nd day after the surgery, the patient had a slight swelling of the upper lip which persisted for 2 days, while the pain was minimal.

On the 4th day, a clinical examination was performed and no edema and hematomas were revealed.

Figure 11C:
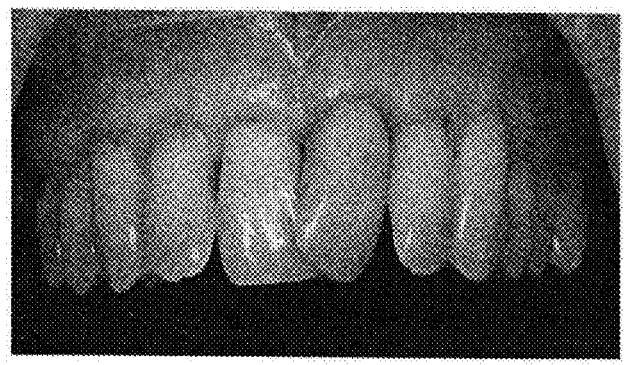
Figure 11D:
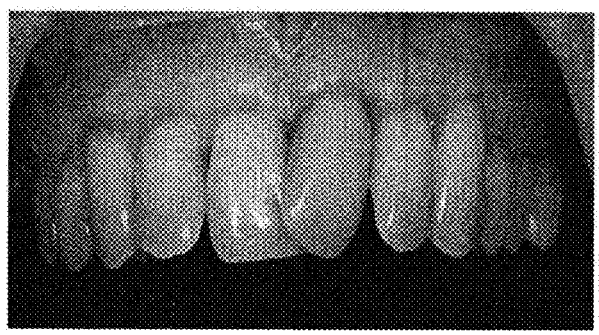
Figure 11E:
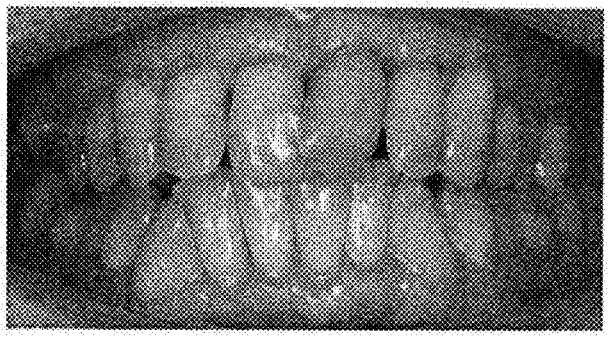

On the 12th day, the sutures were removed. Clinically, a closing of the gingival recessions in the area of 13-23 teeth was revealed (FIG. 11C). The same clinical picture was observed after 1, 3, and 6 months of observation (FIG. 11 D, E).

No complications and adverse events were revealed during the entire period of observation.

CITED REFERENCES

1. Garcia-De La Fuente A. M., Estefania-Fresco R., Marichalar-Mendia X. Complications of harvesting a connective tissue graft from the palate. A retrospective study and description of a new technique. J Clin Exp Dent. 2017; December 1; 9(12):e1439-e1445. doi: 10.4317/jced.54337.
2. McGuire M. and Scheyer E. T. A randomized, double-blind, placebo controlled study to determine the safety and efficacy of cultured and expanded autologous fibroblast injections for the treatment of interdental papillary insufficiency associated with papilla priming procedure. J Periodontol. 2007; 78:4-17.
3. Iordanishvili A. K., Smoljaninov A. B., Zharov E. V. The role of cell technologies in dentistry and maxillofacial surgery. AG-info. 2006; 4:8-11.
4. Saczko J., Dominiak M., Kulbacka J. A simple and established method of tissue culture of human gingival fibroblasts for gingival augmentation. Folia Histochem Cytobiol. 2008:46(1): 117-9.
5. Grudjanov A. I., Zorin V. L., Zorina A. I. et al. Cell technologies in periodontology. Stomatology, 2009; (1): 71-3.
6. Kulakov A. A., Grudjanov A. I., Stepanova I. I. et al. The use of autologous fibroblasts of the human oral mucosa to eliminate gum recessions. Stomatology, 2007, 52-6.
7. Pini-Prato G. P., Rotundo R., Magnani C., Soranzo C. Tissue engineering technology for gingival augmentation procedures: a case report. Int J Periodontics Restorative Dent. 2000; 20:552-59.
8. Pini-Prato G., Rotundo R., Magnani C., Soranzo C., Muzzi L., Cairo F. An autologous cell gyaluronic acid graft technique for gingival augmentation: a case series. J Periodontol., 2003; 74: 262-7.
9. McGuire M. K., Scheyer E. T., Nunn M. E., Lavin P. T. A pilot study to evaluate a tissue-engineered bilayered cell therapy as an alternative to tissue from the palate. J Periodontol., 2008; 79:1847-56.
10. Milinkovic et al. Clinical application of autologous fibroblast cell culture in gingival recession treatment. J Periodontal Res., 2015; 50(3):363-70.
11. Koseoglu et al. Efficacy of collagen membrane seeded with autologous gingival fibroblasts in gingival recession treatment: a randomized, controlled pilot study. J Periodontol., 2013; 84(10): 1416-24.
12. Marx R. Platelet-rich plasma: evidence to support its use. J. Oral Maxillofac. Surg., 2004; 62: 489-96.
13. Ehrenfest D. M., Bielecki T., Mishra A. et al. In search of a consensus terminology in the field of platelet concentrates for surgical use: platelet-rich plasma (PRP), platelet-rich fibrin (PRF), fibrin gel polymerization and leukocytes. Curr Pharm Biotechnol., 2012; 13(7):1131-7.
14. Aroca S., Keglevich T., Barbieri B. et al. Clinical evaluation of a modified coronally advanced flap alone or in combination with a platelet-rich fibrin membrane for the treatment of adjacent multiple gingival recessions: a 6-month study. J. Periodontol., 2009; 80(2):244-52.
15. Cortellini S., Castro A., Temmerman A. et al. L-PRF block for bone augmentation procedure: a proof-of-concept study. J Clin Periodontol., 2018; . . . ??
16. Castro A., Meschi N., Temmerman A. et al. Regenerative potential of leucocyte- and platelet-rich fibrin. Part B: sinus floor elevation, alveolar ridge preservation and implant therapy. A systematic review. J Clin Periodontol., 2017; 44(2):225-34.
17. Ehrenfest D. M., Andia I., Zumstein M. A. et al. Classification of platelet concentrates (Platelet-Rich Plasma-PRP, Platelet-Rich Fibrin-PRF) for topical and infiltrative use in orthopedic and sports medicine: current consensus, clinical implications and perspectives. Muscle, Ligaments and Tendons Journal, 2014; 4(1): 3-9.
18. Schar M., Diaz-Romero J., Kohl S. et al. Platelet-rich concentrates differentially release growth factors and induce cell migration in vitro. Clin Orthop Relat Res., 2015; 473:1635-430.
19. Marenzi G., Riccitiello F., Tia M. et al. Influence of Leukocyte- and Platelet-Rich Fibrin (L-PRF) in the Healing of Simple Postextraction Sockets: A Split-Mouth Study. BioMed Research International, 2015; 1-6. http://dx.doi.org/10.1155/2015/369273.
20. Fujioka-Kobayashi M., Miron R., Hernandez M. et al. Optimized Platelet-Rich Fibrin With the Low-Speed Concept: Growth Factor Release, Biocompatibility and Cellular Response. Journal of Periodontology, 2016; DOI: 10.1902/jop.2016.160443.
21. Fan W., Yang M., Zhang C. et al. Effects of Choukroun's platelet-rich fibrin on human gingival fibroblasts proliferation, migration and type I collagen secretion. Zhonghua Kou Qiang Yi Xue Za Zhi., 2013; 48(2):72-6.
22. Sorrel M., Caplan A. I. Fibroblasts—a diverse population at the center of it all. International Review of Cell and Molecular biology, 2009; 276:161-214.
23. Stephens P. and Genever P. Non-epithelial oral mucosal progenitor cell populations. Oral Diseases, 2007; 13:1-10.
24. Zorin V., Zorina A., Cherkasov V. et al. Clinical-instrumental and morphological evaluation of the effect of autologous dermal fibroblasts administration. J Tissue Eng Regen Med., 2014. doi: 10.1002/term.
25. Hakkinen L., Larjava H., Fournier B. Distinct phenotype and therapeutic potential of gingival fibroblasts. Cytotherapy, 2014; 16:1171-86.
26. McGuire M. C. and Nunn M. E. Evaluation of the safety and efficacy of periodontal applications of a living tissue-engineered human fibroblast-derived dermal substitute. Comparison to the gingival autograft: a randomized controlled pilot study. J. Periodontol., 2005; 76(6):867-80.
27. U.S. Pat. No. 6,878,383, IPC A61A 13/00.
28. Stepanova I. I. Application of fibroblasts in dentistry and implantology. Cell technologies in biology and medicine, 2007; 3:165-8.
29. Chang H., Chi J., Dudoit S. et al. Diversity, topographic differentiation, and positional memory in human fibroblasts. Proc Natl Acad Sci USA, 2009; 99:12877-82.
30. Guo F., Carter D., Mukhopadhyay A., Leask A. Gingival fibroblasts display reduced adhesion and spreading on extracellular matrix: a possible basis for scarless tissue repair? PLoS One., 2011; 6:270-97.
31. Ebisawa K., Kato R., Okada M. et al. Gingival and dermal fibroblasts: their similarities and differences revealed from gene expression. J Biosci Bioeng., 2011; 111:255-8.
32. Fournier B., Larjava H., Häkkinen L. Gingiva as a source of stem cells with therapeutic potential. Stem Cells Dev., 2013; 22:3157-3177.
33. Lorimier S., Hornebeck W., Godeau G. et al. Morphometric studies of collagen and fibrin lattices contracted by human gingival fibroblasts; comparison with dermal fibroblasts. J Dent Res., 1998; 77:1717-29.
34. Brizzi M., Tarone G., Defilippi P. Extracellular matrix, integrins, and growth factors as tailors of the stem cell niche. Curr Opin Cell Biol., 2012; 24:645-51.
35. Gogly B., Naveau A., Fournier B. et al. Preservation of rabbit aorta elastin from degradation by gingival fibroblasts in an ex vivo model. Arterioscler Thromb Vase Biol., 2007; 27:1984-90.
36. Durand E., Fournier B., Couty L. et al. Endoluminal gingival fibroblast transfer reduces the size of rabbit carotid aneurisms via elastin repair. Arterioscler Thromb Vase Biol., 2010; 32:1892-901.
37. Hakkinen L., Larjava H., Koivisto L. Granulation tissue formation and remodeling. Endodontic Topics, 2012; 24:94-129.
38. Dufour A., Overall C. Missing the target: matrix metalloproteinase antitargets in inflammation and cancer. Trends Pharmacol Sci., 2013; 34:233-42.
39. Cappellesso-Fleury S., Puissant-Lubrano B., Apoil P. et al. Human fibroblasts share immunosuppressive properties with bone marrow mesenchymal stem cells. J Clin Immunol., 2010; 30:607-19.
40. Fawzy El-Sayed K. and Dorfer C. Gingival Mesenchymal Stem/Progenitor Cells: A Unique Tissue Engineering Gem. Stem Cells International, 2016; Article ID 7154327, 1-16.
41. Xu X., Chen C., Akiyama K. et al. Gingivae Contain Neural-crest- and Mesoderm-derived Mesenchymal Stem Cells. J Dent Res., 2013; 92(9):825-32.
42. Kobayashi K., Suzuki T., Nomoto Y. et al. Potential of heterotopic fibroblasts as autologous transplanted cells for tracheal epithelial regeneration. Tissue Eng., 2007; 13:2175-84.
43. Karring T., Lang N., Loe H. The role of gingival connective tissue in determining epithelial differentiation. J Periodont Res., 1975; 10:1-11.
44. Mah W., Jiang G., Olver D. et al. Human gingival fibroblasts display a non-fibrotic phenotype distinct from skin fibroblasts in three-dimensional cultures. PLoS One., 2014; 9:907-15.
45. Parsonage G., Filer A., Haworth O. et al. A stromal address code defined by fibroblasts. Trends Immunol., 2005; 26:150-6.120.
46. Hakkinen L., Uitto V. J., and Larjava H. Cell biology of gingival wound healing. Periodontol., 2000; 24:127-52.
47. Prato G., Rotundo R., Magnani C. et al. An autologous cell hyaluronic acid graft technique for gingival augmentation: a case series. J Periodontol., 2003; 74:262e7.
48. Chhetri D., Berke G. Injection of cultured autologous fibroblasts for human vocal fold scars. Laryngoscope, 2011; 121:785-92.
49. Linard C., Tissedre F., Busson E. et al. Therapeutic Potential of Gingival Fibroblasts for Cutaneous Radiation Syndrome: Comparison to Bone Marrow-Mesenchymal Stem Cell Grafts. STEM CELLS AND DEVELOPMENT, 2015; 1-12. Inc. DOI: 10.1089/.
50. Freshney J. A Culture of Animal Cells., Freshney J. 3rd edition, Wiley Liss Inc., New York, 1994.

The invention claimed is:

1. A method for making a biotransplant, comprising:
introducing autologous fibroblasts isolated from an oral mucosa of a patient into a platelet-rich fibrin (PRF) membrane, thereby producing the biotransplant,
wherein the autologous fibroblasts are suspended in a suitable medium at a concentration of from $5 \times 10^6$ to $20 \times 10^6$ cells/ml, and
wherein the introducing comprises linear retrograde needle injection of the suspended autologous fibroblasts into the PRF membrane.

2. The method of claim 1,
wherein the retrograde needle injection comprises inserting a needle into a thickness of the PRF membrane and making a first puncture and then a series of punctures linearly aligned or arrayed with the first puncture each spaced at a distance of 0.2 to 0.33 mm from a prior puncture, and
wherein an amount of from 50 to 100 μL of a 1 ml suspension of the autologous fibroblasts is injected into each puncture until an entire amount of the 1 ml suspension has been injected into the punctures.

3. The method of claim 1, wherein the autologous fibroblasts are obtained from cryopreserved autologous fibroblasts.

4. The method of claim 1, further comprising obtaining the autologous fibroblasts from a biopsy sample of the oral mucosa of the patient.

5. A method of treatment of a periodontal tissue, comprising:

introducing a biotransplant into a damaged part of the gingiva using a surgery, wherein the biotransplant is obtained by a method comprising:

introducing autologous fibroblasts isolated from an oral mucosa of a patient into a platelet-rich fibrin (PRF) membrane, thereby producing the biotransplant, wherein the autologous fibroblasts are suspended in a suitable medium at a concentration of from $5\times10^6$ to $20\times10^6$ cells/ml, wherein the introducing comprises linear retrograde needle injection of the suspended autologous fibroblasts into the PRF membrane, wherein the retrograde needle injection comprises inserting a needle into a thickness of the PRF membrane and making a first puncture and then a series of punctures linearly aligned or arrayed with the first puncture each spaced at a distance of 0.2 to 0.33 mm from a prior puncture, and wherein an amount of from 50 to 100 µL of a 1 ml suspension of the autologous fibroblasts is injected into each puncture until an entire amount of the 1 ml suspension has been injected into the punctures.

6. A method for treating a periodontal tissue comprising grafting a biotransplant over a periodontal tissue of a subject in need thereof, wherein the biotransplant is obtained by a method comprising:

introducing autologous fibroblasts isolated from an oral mucosa of a patient into a platelet-rich fibrin (PRF) membrane, thereby producing the biotransplant, wherein the autologous fibroblasts are suspended in a suitable medium at a concentration of from $5\times10^6$ to $20\times10^6$ cells/ml, wherein the introducing comprises linear retrograde needle injection of the suspended autologous fibroblasts into the PRF membrane, wherein the retrograde needle injection comprises inserting a needle into a thickness of the PRF membrane and making a first puncture and then a series of punctures linearly aligned or arrayed with the first puncture each spaced at a distance of 0.2 to 0.33 mm from a prior puncture, and wherein an amount of from 50 to 100 µL of a 1 ml suspension of the autologous fibroblasts is injected into each puncture until an entire amount of the 1 ml suspension has been injected into the punctures.

7. The method of claim 6, wherein the periodontal tissue comprises a damaged hard gingival tissue, soft gingival tissue, or a combination thereof.

8. The method of claim 6, wherein the periodontal tissue has been damaged by oral surgery.

9. The method of claim 6, wherein the periodontal tissue comprises a gingival recession or a gingival wound or burn.

10. The method of claim 6, wherein the subject has insufficient connective tissue in the palate for a connective tissue transplant (CTT).

11. The method of claim 6, wherein the subject has periodontitis.

12. The method of claim 6, wherein the subject has trauma of tissues around an exposed root of a tooth.

13. The method of claim 6, wherein the subject has trauma of periodontal tissues around an implant.

14. The method of claim 6, wherein the subject is in need of soft tissue augmentation prior to orthodontic treatment.

15. The method of claim 6, wherein the subject exhibits allergological alertness to proteins of foreign origin.

16. A biotransplant obtained by a method comprising:

introducing autologous fibroblasts isolated from an oral mucosa of a patient into a platelet-rich fibrin (PRF) membrane, thereby producing the biotransplant, wherein the autologous fibroblasts are suspended in a suitable medium at a concentration of from $5\times10^6$ to $20\times10^6$ cells/ml, wherein the introducing comprises linear retrograde needle injection of the suspended autologous fibroblasts into the PRF membrane, wherein the retrograde needle injection comprises inserting a needle into a thickness of the PRF membrane and making a first puncture and then a series of punctures linearly aligned or arrayed with the first puncture each spaced at a distance of 0.2 to 0.33 mm from a prior puncture, and wherein an amount of from 50 to 100 µL of a 1 ml suspension of the autologous fibroblasts is injected into each puncture until an entire amount of the 1 ml suspension has been injected into the punctures.

* * * * *